(12) United States Patent
Reinhron et al.

(10) Patent No.: US 6,587,193 B1
(45) Date of Patent: Jul. 1, 2003

(54) INSPECTION SYSTEMS PERFORMING TWO-DIMENSIONAL IMAGING WITH LINE LIGHT SPOT

(75) Inventors: Silviu Reinhron, Mevaseret-Zion (IL); Gilad Almogy, Givatayim (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/309,358

(22) Filed: May 11, 1999

(51) Int. Cl.$^7$ .............................................. G01N 21/00
(52) U.S. Cl. .................................................. 356/237.5
(58) Field of Search ........................ 356/237.1, 239.1, 356/239.2, 239.3, 237.7, 239.7, 239.8, 237.2, 237.3, 237.4, 237.5, 345, 349, 354, 351; 250/572

(56) References Cited

U.S. PATENT DOCUMENTS

| | | | |
|---|---|---|---|
| 5,274,434 A | | 12/1993 | Morioka et al. ............. 356/237 |
| 5,486,919 A | * | 1/1996 | Tsuji et al. .................. 356/349 |
| 5,631,733 A | | 5/1997 | Henley ........................ 356/237 |
| 5,748,305 A | * | 5/1998 | Shimono et al. ............. 356/237 |
| 5,798,831 A | * | 8/1998 | Hagiwara .................. 356/237.1 |
| 5,856,868 A | | 1/1999 | Kato et al. ................... 356/237 |
| 5,864,394 A | * | 1/1999 | Jordan, III et al. ........ 356/237.1 |
| 5,883,710 A | * | 3/1999 | Nikoonahad et al. ..... 356/237.2 |
| 5,889,593 A | | 3/1999 | Bareket ....................... 356/445 |
| 5,903,378 A | * | 5/1999 | Takano et al. ............... 359/201 |
| 5,940,175 A | * | 8/1999 | Sun ........................... 356/237.3 |
| 6,256,093 B1 | * | 7/2001 | Ravid et al. .............. 356/237.2 |

FOREIGN PATENT DOCUMENTS

| | | |
|---|---|---|
| WO | WO 98/20327 | 5/1998 |
| WO | WO 99/06823 | 2/1999 |
| WO | WO 99/14575 | 3/1999 |
| WO | WO 99/38002 | 7/1999 |

\* cited by examiner

Primary Examiner—Michael P. Stafira
(74) Attorney, Agent, or Firm—Sughrue Mion, PLLC.

(57) ABSTRACT

A wafer inspection system is described. The wafer is illuminated by an elongated "linear" or "line spot." The "line spot" is basically an elongated illumination on the wafer surface, such that it covers several pixels aligned to form a line. The linear spot is held stationary with respect to one direction, but the wafer is scanned under it in the other direction. Thus, a two dimensional area is covered and can be imaged. Imaging is preferably performed using a sensor array, such as a line CCD. In the preferred embodiment, two linear spots are used in conjunction with two line CCD's. When inspecting a patterned wafer, the linear spots are projected at complementing 45° angles to the "streets and avenues" axis of the wafer.

14 Claims, 5 Drawing Sheets

INSPECTION SYSTEMS PERFORMING TWO-DIMENSIONAL IMAGING WITH LINE LIGHT SPOT

FIELD OF THE INVENTION

This invention relates to the systems for inspection of substrates, especially semiconductor wafers and reticles. More specifically, the invention relates to a novel system which illuminates lines of pixels on the substrate, and images reflected and/or scattered light from the lines.

BACKGROUND OF THE INVENTION

Figure 1:
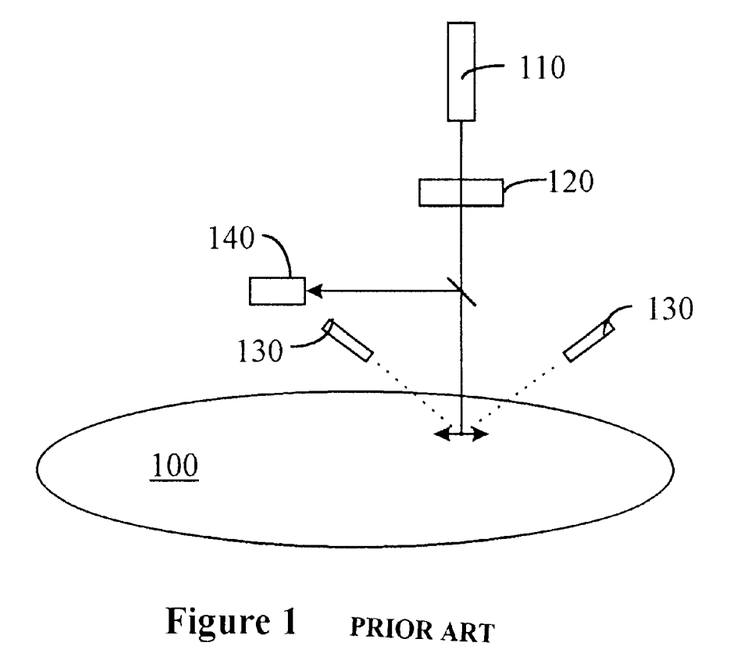
FIG. 1 is a schematic representation of prior art wafer inspection system using normal illumination.
Figure 2:
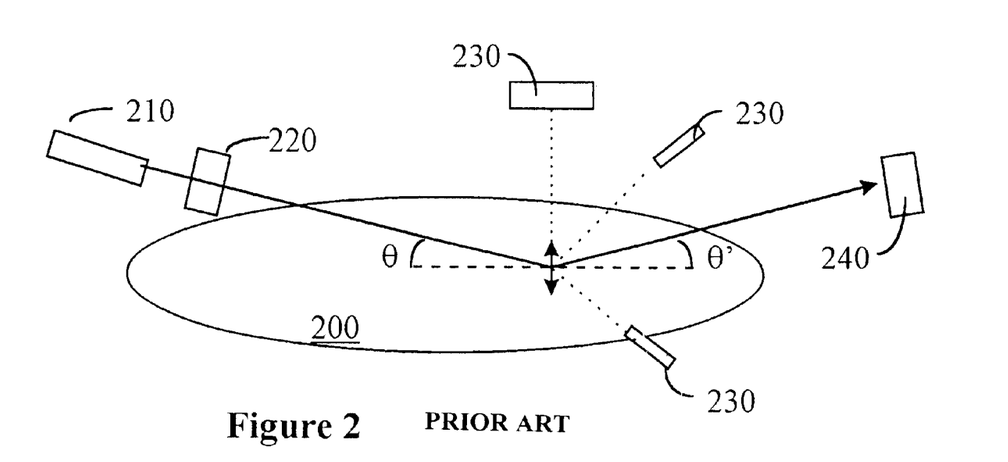
FIG. 2 is a schematic representation of another prior art wafer inspection system, using grazing angle illumination.

Several systems are known in the art for the inspection of wafers and reticles. Two examples of such systems are depicted in FIGS. 1 and 2. In the system exemplified in FIG. 1, the wafer 100 is illuminated with a light beam emanating from a light source 110 and reaching the wafer at 90° angle (generally referred to as normal illumination). Preferably, light source 100 provides coherent light, i.e., source 100 may be a laser source. The light beam is scanned over the wafer by a scanner 120, typically an acousto-optical scanner (AOD) or a rotating mirror, in the direction marked by the double-headed arrow. The wafer 100 is moved in the perpendicular direction by moving the stage upon which the wafer rests. Thus, a two dimensional area of the wafer can be scanned by the light beam.

Since the wafer has basically a mirror-like top surface, the light beam specularly reflects back per Snell's law at 180°. This specularly reflected light is collected by a light sensor 140 and its signal is used to obtain a "bright field" image, i.e., an image created from specularly reflected light. However, whenever the light beam hits an irregularity on the wafer, such as a particle or etched pattern, the light scatters in various directions. Some of the diffracted/scattered light is then collected by the light sensors 130, and their signal is used to obtain a "dark field" image, i.e., an image created from diffracted/scattered light. Thus, when the wafer has no pattern on it (e.g., blank wafer), the irregularities appear in the dark field image as stars in a dark sky. When the wafer has a pattern on it, the irregularities cause a scattered light which deviates from the normal diffraction caused by the pattern.

In the system exemplified in FIG. 2, the wafer 200 is illuminated by a light beam emanating from light source 210, but reaching the wafer at a shallow angle, generally referred to as grazing illumination. The light beam is scanned over the wafer by a scanner 220, typically an acousto-optical scanner or a rotating mirror, in the direction marked by the double-headed arrow. The wafer 200 is moved in the perpendicular direction by moving the stage upon which the wafer rests. Thus, a two dimensional area of the wafer can be scanned by the light beam.

Since the light reaches the wafer at a grazing angle θ, its specular reflection is at a corresponding angle, θ', according to Snell's law. This light can be collected by sensor 240, and its signal is used to create the bright field image. Any diffracted/scattered light is collected by sensors 230, the signal of which is used to create dark field images.

It should be appreciated that in the above exemplified systems, with respect to each sensor the image data is acquired serially. That is, each two dimensional image, whether bright or dark field, is constructed by acquiring signals of pixel after pixel, per the scanned light beam. This is time consuming serial operation, which directly affects the throughput of such systems. Moreover, the scan speed of such systems is limited by the scanner's speed (i.e., the band-width for an acousto-optic scanner) and by the electronics that support the detectors, e.g., the PMT (Photo-Multiplier Tube). Thus, a need exists to develop a system that does not utilize a scanned light beam.

Looking forward, as design rules shrink, the importance of detecting increasingly small irregularities becomes paramount. With design rules such as 0.18 and 0.15 $\mu$m, very small irregularities, such as particles of sub-micron size, can be killer defects and cause the device to malfunction. However, in order to detect such small irregularities, one needs to use a very small wavelength light source, such as ultra violate (UV) or deep ultra violate (DUV) light source. This presents at least two crucial problems: first, optical elements operating in the DUV regime are expensive and, second, small short wave implies small spot size of the light beam; thus, the scanning speed and collection data rate need to be increased.

Currently, commercially available AOD that can support a scanning for a DUV beam have a very limited performance. Additionally, even if such AOD can be developed, at present it is unclear whether it could withstand the energy levels required for obtaining a high resolution image using a DUV light beam. Thus, reducing the power level may also dictate use of a slower scanning AOD. Therefore, future systems may also require implementations that do not relay on beam scanning.

SUMMARY OF THE INVENTION

According to the present invention, the wafer is illuminated by an elongated "linear" or "line spot." The "line spot" is basically an elongated illumination on the wafer surface, such that it covers several pixels aligned to form a line. In the preferred embodiment, the number of pixels in the linear spot is on the order of thousands. The linear spot is held stationary with respect to one direction, but the wafer is scanned under it in the other direction. Thus, a two dimensional area is covered and can be imaged. Imaging is preferably performed using a sensor array, such as a line CCD. In the preferred embodiment, two linear spots are used in conjunction with two line CCD's. The detected lateral pixel size (along the narrow dimension of the line) is determined by the illumination line width. The detected pixel size along the longitudinal direction is determined by the resolution of the collection optics and the line CCD camera pixel size. When inspecting a patterned wafer, the linear spots are projected at complementing 45° angles to the "streets and avenues" axis of the wafer.

The present invention is advantageous in that it enables much faster data acquisition rate. Furthermore, it is operable with short wavelengths, such as UV or deep UV illumination. Notably, the inventive system does not require a scanning mechanism. Other advantages of the invention will appear as the description proceeds.

DETAILED DESCRIPTION OF PREFERRED EMBODIMENTS

Before, proceeding with the description of the preferred embodiments, it should be noted that any of the embodiments are suitable for inspection of un-patterned wafers. However, several notable advantages of the invention are particularly useful for the more complicated task of patterned wafers inspection. Therefore, much of the discussion presented herein relates to patterned wafers.

Figure 3:
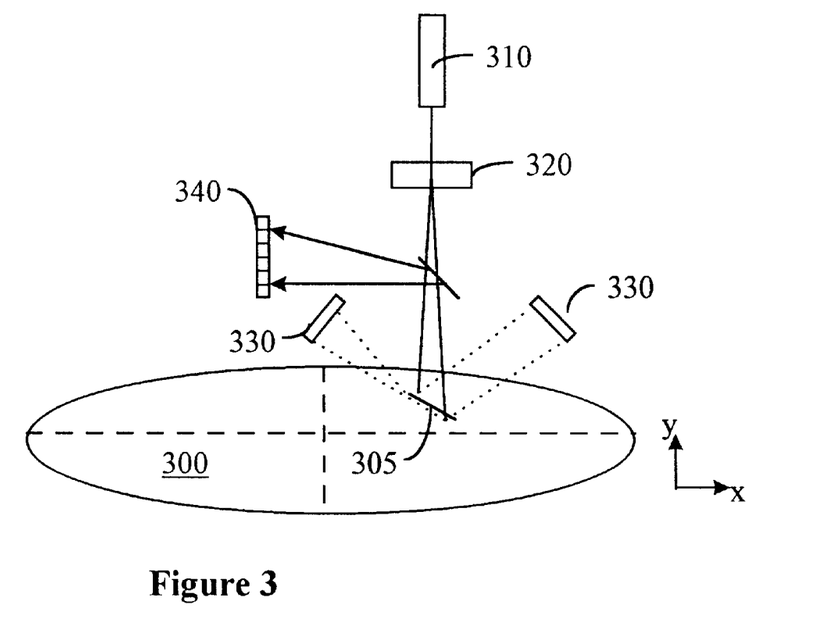
FIG. 3 is a schematic representation of a first embodiment of the present invention.

FIG. 3 depicts a simplified version of the present invention. The wafer 300 is illuminated by a linear spot 305 impinging in normal direction with respect to the wafer, created by a light source 310 and suitable optics 320. In the preferred embodiment, the linear spot is held stationary, while the wafer is scanned in the y direction by moving the stage. Thus, a two dimensional strip is scanned over the wafer without the need for scanning the spot in the x direction. The dimensions of the scanned strip are defined by the effective size of the linear spot.

Specularly reflected light from the linear spot is then imaged on a sensor array 340, and diffracted light is imaged on sensor arrays 330. Thus, bright and dark field images can be obtained at a fast rate, since the images are sampled one line at a time, rather than one pixel at a time. That is, each sampling of a sensor array provides pixel data for an entire line, the width of the scanned strip. Since sensor arrays of 1024, 2048 and 4096 pixels are widely available off the shelf, the speed of image acquisition can be dramatically increased using the invention. For example, using a sensor array having 2048 pixels with 16 channels, one can achieve acquisition speed of 400 Mb/s.

Another feature of the present invention is exemplified in FIG. 3. As is well known, one difficulty in inspecting patterned wafers is that features constructed on the wafer, such as metal lines, also diffract light. This causes at least two problems. As far as bright field image is concerned, strong reflections from metals line saturate the light sensor, so that irregularities laying close to the line may go undetected. As far as dark field is concerned, diffraction from metal lines can be mistaken by the system for irregularities. Thus, in order to avoid these problems, in the preferred embodiment depicted in FIG. 3, the linear spot is projected at 45° angle to the streets and avenues (shown in broken lines) of the patterned wafer. Consequently, with respect to the bright field image, instantaneous reflections from metal lines are minimized and, with respect to dark field images, diffraction from metal lines is avoided in the direction of the sensors.

Figure 4:
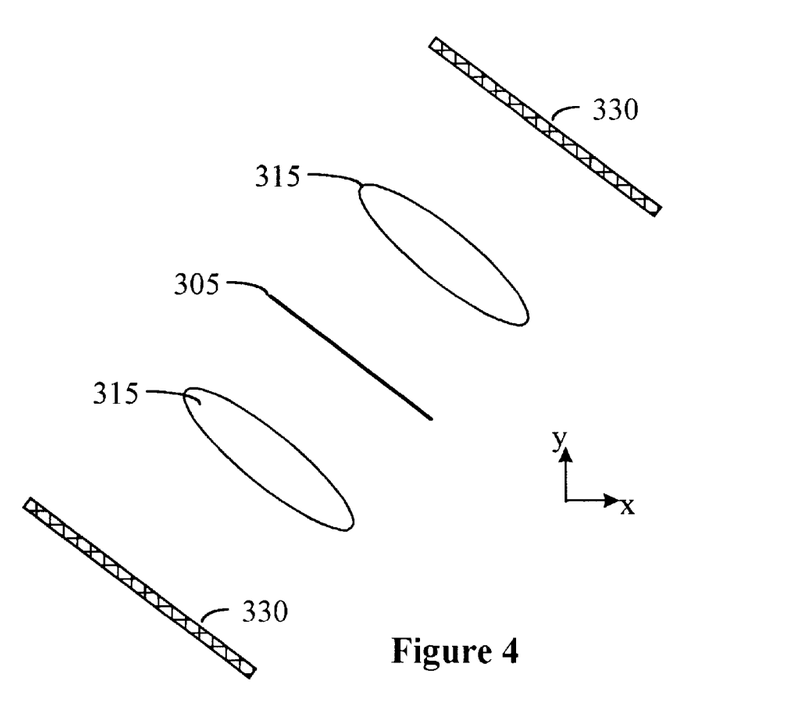
FIG. 4 is a top view of the elements of the system depicted in FIG. 3, which are relevant for the understanding of the dark field imaging.

The above feature is exemplified in more detail in FIG. 4, which is a top view of the inventive system of FIG. 3. Specifically, linear spot 305 is depicted as being at 45° angle to the x-y axis (i.e., the streets and avenues directions of the wafer). On either side of the linear spot, objectives 315 are used to image the spot onto the line sensors 330. Of course, so long as no irregularity is present, i.e., no light is diffracted, the image projected by the objectives 315 would mostly be dark. However, when irregularity is present, the light hitting it will be scattered and imaged onto the sensor arrays 330. Depending on the size of the irregularity, the bright image can appear on only a single or on several elements of the sensor array. The detected pixel size is determined by two main factors: the illumination line width and the collection optics resolution. The illumination line width is determined by the numerical aperture of the cylindrical lens. However, the detected pixel size in the longitudinal direction is determined by the numerical aperture of the collection optics and the line CCD camera pixel size.

Figure 5:
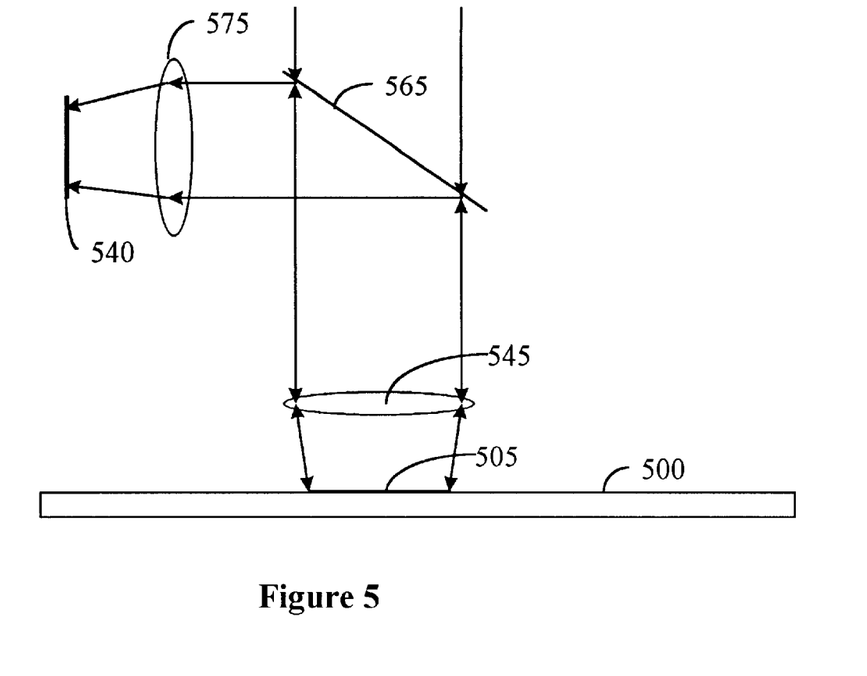
FIG. 5 is a side view of the elements of the system depicted in FIG. 3, which are relevant for the understanding of the bright field imaging.

Sampling of the bright field image is exemplified in FIG. 5, in which elements relating to dark field imaging have been omitted for clarity. Specifically, the illumination light passes through a beam splitter 565 and objective 545. When the light is reflected, it again passes through the objective 545, but this time it is reflected by the mirror 565 onto lens 575. Lens 575 images the linear spot onto the sensor array 540.

While the system thus far described has a vastly increased throughput, in its preferred embodiment it includes two linear spots imaged onto four dark field sensor arrays. This is exemplified in FIG. 6, which depicts how the prior art system of FIG. 2 can be modified to include the inventive system. However, it should be appreciated that all the embodiments described herein can be equally applied to any prior art system, including those depicted in FIGS. 1 and 2.

Figure 6:
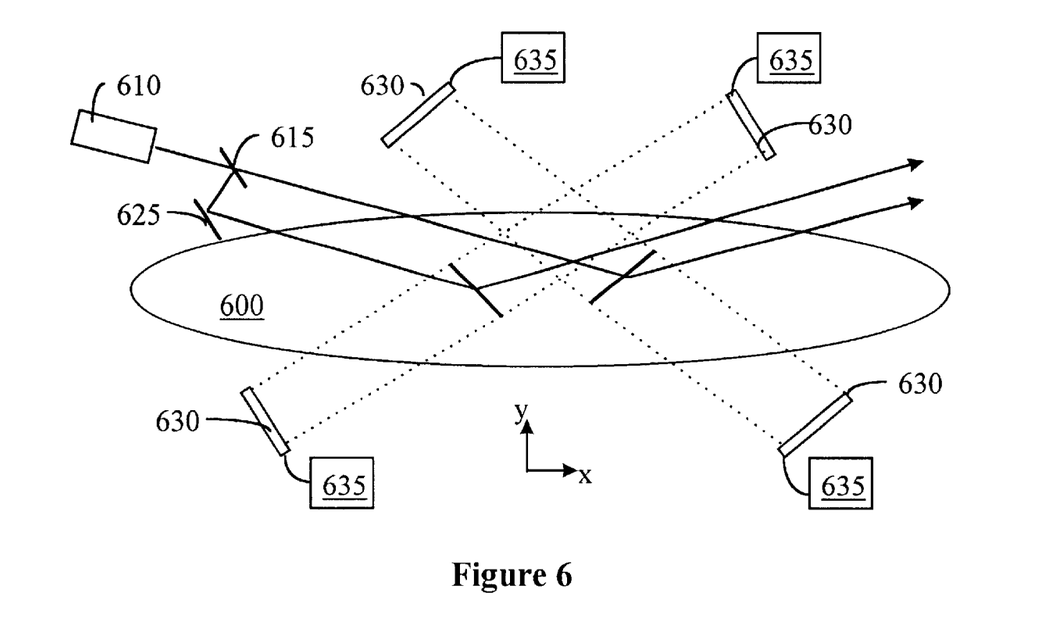
FIG. 6 is a schematic representation of another embodiment of the present invention, employing four dark field detectors.

In FIG. 6, the beam provided from light source 610 is split by beam splitter 615. Part of the light is allowed to continue and illuminate a first linear spot, while the remaining light is reflected by mirror 625 to illuminate a second linear spot. The linear spots are oriented at 45° with respect to the x-y axis of the wafer, but at 90° to each other. Two pairs of sensor arrays image one linear array, while another pair images the other. This configuration provides imaging of each pixel from four different dark field perspectives.

However, in order to correlate the various perspectives, one need to account for the different imaging locations of the four sensors 630. That is, in inspection systems it is known to perform a die-to-die or a cell-to-cell comparison of each pixel to detect defects. Thus, for each particular pixel location defined on the wafer, the various perspective images are compared to similar images of a corresponding location in the neighboring preceding and proceeding dies or cells. Thus, for each comparison operation, the images of the specific pixel location need to be correlated. This operation is schematically illustrated in FIG. 6 by showing each sensor 630 connected to a delay line 635. Of course, one may instead perform the delay using an algorithm rather than actual electronic delay. That is, since the collected data is stored in memory, for each pixel location the algorithm can fetch the appropriate data from the appropriate locations in the memory.

It should be appreciated that the two linear spots need not be separated in space and can be crossed instead. However, such an arrangement is not very desirable since it will have higher noise caused by stray light. That is, while one line spot will be properly imaged onto the sensor array, some additional light from the other line spot will also enter the imaging system and may reduce the signal to noise ratio. Therefore, the configuration as shown is preferable.

Additionally, a bright field sensor array may be added, although it has been omitted from FIG. 6 for clarity. Of course, the inventive system is easily adaptable to inspection systems using UV or DUV coherent light, since there's no limitation on scanning capability and rate.

For the preferred embodiment, it is possible to use off the shelf line CCD's. Such CCD's are currently capable of acquisition rates of 400 Mb/sec, provided in 16 parallel channels, i.e., 25 Mb/sec/channel. While such data rates are several times the current data acquisition rates, the line CCD's can be custom designed to achieve data rates on the order of 1 Gb/sec and even further increase the acquisition rate. Moreover, since the data from the line CCD's is provided in 16 parallel channels, it reduces the load on the collection electronics, since each line can be provided with its own electronics, thus each electronics package would have to handle only one sixteenth of the overall data rate. Of course, the custom designed CCD's can be designed with a larger number of channels, suitable for the particular system designed.

Figure 7:
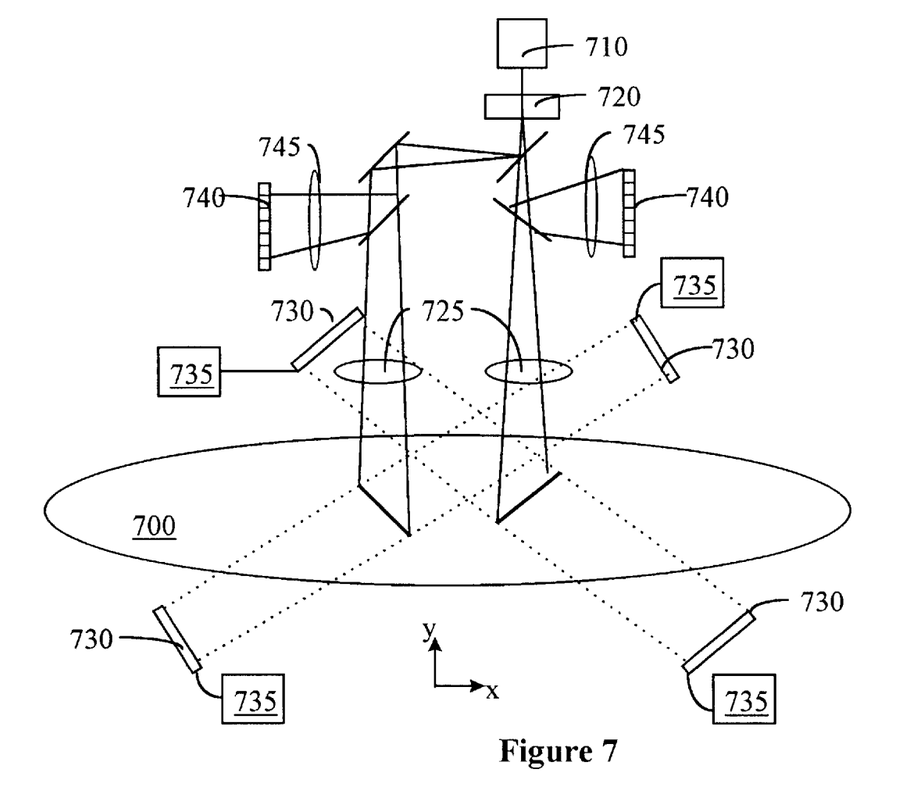
FIG. 7 is a schematic representation of the preferred embodiment of the present invention, employing dark and bright field detectors.
Figure 8:
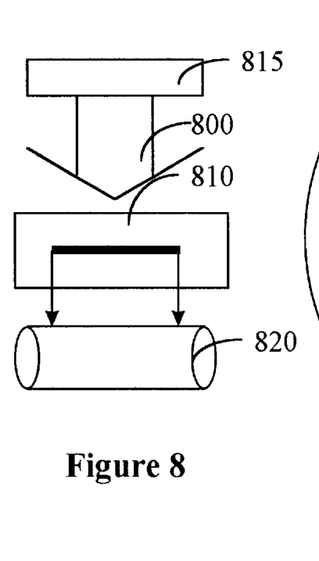
FIG. 8 exemplifies an optical system for converting the light beam into a linear beam.

The preferred embodiment of the present invention is depicted in FIG. 7. Specifically, FIG. 7 depicts a manner of modifying the system of FIG. 1 to include the features of the present invention. The system of FIG. 7 includes normal illumination from a light source 710. The light from the light source 710 is made into a linear beam by optics 720. Optics 720 can generally comprise elements such as a beam expander, a cylindrical lens, and a cylindrical lens in combination with a slit aperture. An exemplary optics 720 is depicted in FIG. 8. Specifically, light from a coherent illumination source is made into an expanded beam 800 by beam expander 815. The expanded beam 800 is passed through a slit aperture 810, and then through a cylindrical lens 820. Thus, a spatially linear beam is obtained. The beam is then split into two beams, each for illuminating one linear spot. Of course, the beam can be first split, and then passed through two optics system to form each beam into a linear beam.

As depicted in FIG. 7, four dark field light sensor arrays are employed to obtain four dark field perspective. As in FIG. 6, the sensor arrays are coupled to delay lines 735, which are implemented in software, hardware, or combination thereof. Additionally, in FIG. 7 two bright field sensor arrays are depicted, to obtain two bright field images; however, it is envisioned that a single bright field sensor array would be sufficient.

Figure 9:
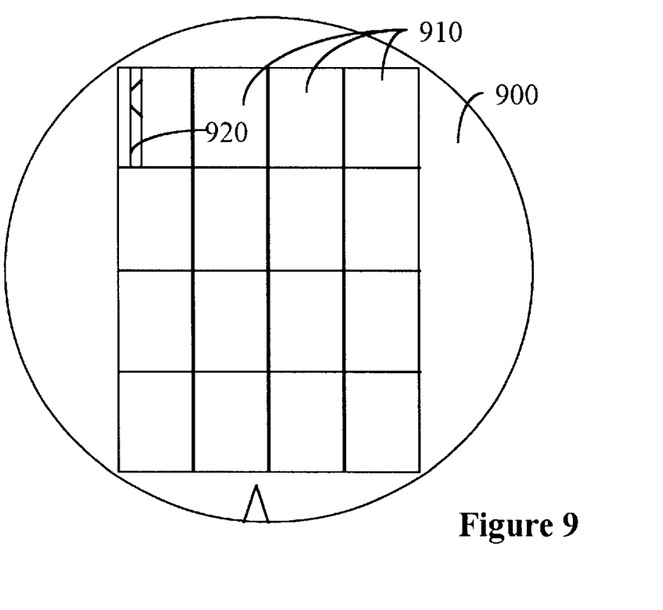
FIG. 9 depicts a manner of two-dimensional imaging of a wafer.

In FIG. 7, a two dimensional image is acquired by moving the wafer in the x direction. Specifically, when inspecting a patterned wafer using a die-to-die method, it is preferred to obtain two-dimensional "strip" images. This is exemplified in FIG. 9. A patterned wafer 900 includes a plurality of dies 910. Each die is imaged by imaging two-dimensional strips 920. The strips are imaged by two line spot illumination, and motions of the wafer in one direction. Thus, the width of the strip corresponds to the sensor array's size, i.e., the number of pixels imaged width-wise corresponds to the number of sensors in the sensor array. The length of the strip can be set according to the application. In a die-to-die comparison, the length of the strip can be set to cover, for example, three dies.

Figure 10:
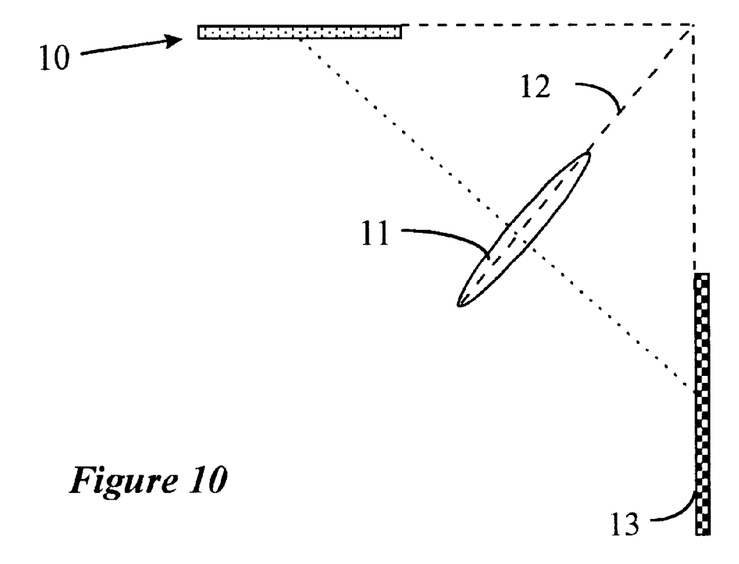
FIGS. 10 and 11 depict two arrangement of Scheimpflug imaging.
Figure 11:
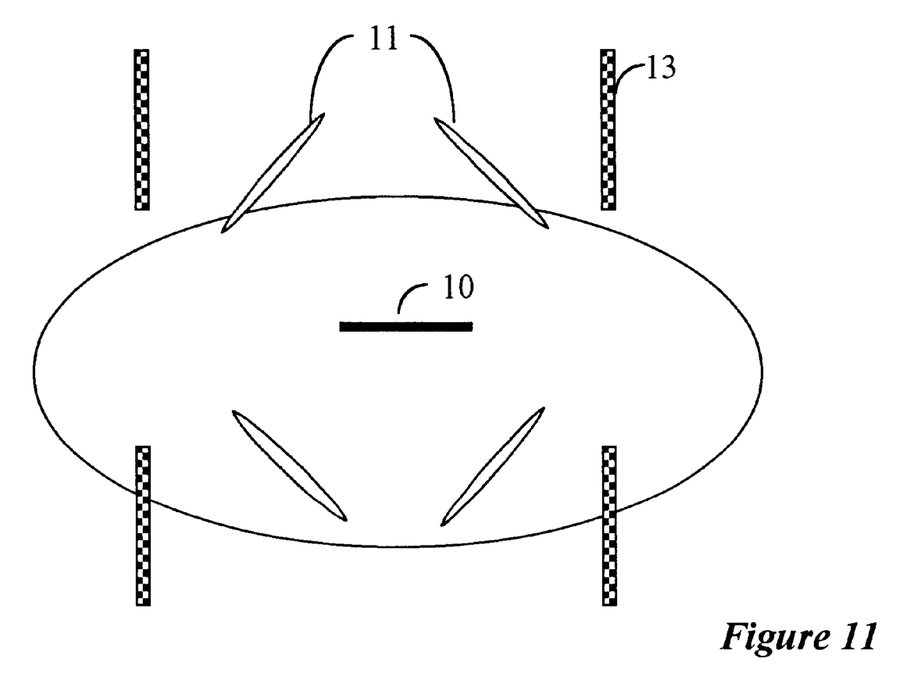

Another possible configuration for imaging the scattered light from an illuminated line onto a line CCD is schematically depicted in FIGS. 10 and 11. In this configuration the illumination line 10 is oriented in parallel to one of the die sides. The scattered light is still collected in an angle of 45 degrees with respect to the streets and alleys of the die because of signal to noise issue discussed before. This could be achieved by using Scheimpflug imaging configuration (reference: Rudolf Kingslake, "Optical System Design", Page 58, 270), i.e. the collection imaging lens 11 should be placed in a position in space so that its median plane 12 is perpendicular to the light scattered into the desired direction (45 degrees). The line CCD 13 is oriented so that the continuation of the line CCD and the illumination line cross each other on the median plane. In such a configuration four line CCD can simultaneously collect the scattered light, and there is no need for two illumination lines.

While embodiments of the invention have been described by way of illustration, it will be apparent that the invention can be carried into practice with many modifications, variations and adaptations without departing from the scope and spirit of the invention, as defined by the appended claims.

What is claimed is:

1. Method for the illumination of a two dimensional area on a substrate, comprising:
   illuminating a line spot on the substrate;
   scanning the substrate in a single direction;
   collecting reflected light at a first angle with respect to a normal to said substrate; and
   collecting scattered light at a second angle with respect to said normal to said substrate; and
   illuminating the substrate with a second line spot oriented at 90° with respect to the line spot.

2. The method according to claim 1, wherein, the step of scanning comprises moving the substrate in a predetermined direction as it is being illuminated.

3. The method according to claim 1, wherein the step of scanning comprises moving the line spot across the substrate in the y direction.

4. The method according to claim 1, wherein the line spot is oriented at 45° with respect to a normal to said substrate.

5. The method according to claim 1, further comprising imaging light reflected from the line spot onto at least one sensor array.

6. The method according to claim 1, further comprising imaging light scattered from the line spot onto at least one sensor array.

7. The method according to claim 1, further comprising imaging light reflected from at least one of the line spot and second line spot onto at least one sensor array.

8. The method according to claim 1, further comprising imaging light scattered from the line spot onto at least one sensor array and imaging light diffracted from the second line spot onto at least one another sensor array.

9. A system for two dimensional scanning of a substrate, comprising:
   a light source providing a light beam;
   a conversion system converting the light beam into a main line beam;
   a beam splitter splitting the main line beam into a first and a second line beams;
   a first optical system projecting the first line beam onto the substrate to illuminate the substrate with a first line spot;
   a second optical system projecting the second line beam onto the substrate to illuminate the substrate with a second line spot;
   a scanning system providing a relative displacement between the first and second line beams and the substrate; and,
   a first sensor array associated with the first line spot; and
   a second sensor array associated with the second line spot.

10. The system of claim 9, wherein said conversion system comprises a cylindrical lens.

11. The system of claim 9, wherein said conversion system comprises a slit aperture.

12. The system of claim 9, wherein said second line spot is oriented at ninety degrees to the first line spot.

13. The system of claim 9, wherein said first and second sensor arrays comprise line CCD's.

14. A system for two dimensional imaging of a substrate having two perpendicular axis defined thereon, comprising:

a light source providing a light beam;

a conversion system converting the light beam into a main line beam;

a beam splitter splitting the main line beam into a first and a second line beams;

a first optical system projecting the first line beam onto the substrate to illuminate the substrate with a first line spot positioned at 45° to the axis;

a second optical system projecting the second line beam onto the substrate to illuminate the substrate with a second line spot, positioned at 90° to the first line spot;

a scanning system providing a relative displacement between the first and second line beams and the substrate; and, a first sensor array associated with the first line spot; and a second sensor array associated with the second line spot.

\* \* \* \* \*

UNITED STATES PATENT AND TRADEMARK OFFICE
CERTIFICATE OF CORRECTION

PATENT NO.     : 6,587,193 B1
DATED          : July 1, 2003
INVENTOR(S)    : Silviu Reinhorn and Gilad Almogy It is certified that error appears in the above-identified patent and that said Letters Patent is hereby corrected as shown below:

<u>Title page,</u>
Item [12], delete "Reinhron", and insert -- Reinhorn --; and
Item [75], delete "Reinhron", and insert -- Reinhorn --.

Signed and Sealed this

Ninth Day of September, 2003

JAMES E. ROGAN
*Director of the United States Patent and Trademark Office*